(12) United States Patent
Li

(10) Patent No.: US 11,324,806 B2
(45) Date of Patent: May 10, 2022

(54) SUSTAINED DELIVERY OF A GROWTH DIFFERENTIATION FACTOR

(71) Applicant: Warsaw Orthopedic, Inc., Warsaw, IN (US)

(72) Inventor: Ping Li, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 79 days.

(21) Appl. No.: 16/165,759

(22) Filed: Oct. 19, 2018

(65) Prior Publication Data

US 2020/0121759 A1 Apr. 23, 2020

(51) Int. Cl.

| | | |
|---|---|---|
| *A61K 38/18* | (2006.01) | |
| *A61K 9/08* | (2006.01) | |
| *A61P 19/08* | (2006.01) | |
| *A61M 5/142* | (2006.01) | |
| *A61P 19/00* | (2006.01) | |

(52) U.S. Cl.
CPC ............ *A61K 38/1875* (2013.01); *A61K 9/08* (2013.01); *A61M 5/14276* (2013.01); *A61P 19/00* (2018.01); *A61P 19/08* (2018.01); *A61M 2210/02* (2013.01); *A61M 2250/00* (2013.01)

(58) Field of Classification Search
CPC ...... A61K 38/1875; A61K 38/18; A61K 9/08; A61L 27/24; A61P 19/08
See application file for complete search history.

(56) References Cited

U.S. PATENT DOCUMENTS

| | | |
|---|---|---|
| 6,281,195 B1 | 8/2001 | Rueger et al. |
| 6,406,711 B1 | 6/2002 | Lee et al. |
| 6,899,716 B2 | 5/2005 | Cragg |
| 7,147,839 B2 | 12/2006 | Sampath et al. |
| 7,485,617 B1 * | 2/2009 | Pohl ..................... C07K 14/475 514/1.1 |
| 7,608,580 B2 | 10/2009 | Kim et al. |
| 7,723,291 B2 | 5/2010 | Beals et al. |
| 7,947,649 B2 | 5/2011 | Su et al. |
| 8,455,436 B2 | 6/2013 | Byers et al. |
| 8,524,662 B2 | 9/2013 | Byers et al. |
| 8,685,432 B2 | 4/2014 | Evans et al. |
| 8,871,710 B2 | 10/2014 | Pohl et al. |
| 8,945,872 B2 | 2/2015 | Scher et al. |
| 9,169,308 B2 | 10/2015 | Scher et al. |
| 9,308,190 B2 | 4/2016 | Li et al. |
| 9,480,649 B2 | 11/2016 | Hansom et al. |
| 9,540,429 B2 | 1/2017 | Scher et al. |
| 9,631,003 B2 | 4/2017 | Scher et al. |
| 9,914,758 B2 | 3/2018 | Scher et al. |
| 2004/0220101 A1 | 11/2004 | Ferree |
| 2005/0112091 A1 * | 5/2005 | DiMauro ............ A61B 17/3472 424/85.1 |
| 2009/0061002 A1 * | 3/2009 | Venbrocks ............ A61L 27/425 424/489 |
| 2009/0259023 A1 * | 10/2009 | Su ......................... A61P 19/08 530/350 |
| 2010/0015230 A1 | 1/2010 | Ron |
| 2010/0184659 A1 | 7/2010 | Jaworowicz |

FOREIGN PATENT DOCUMENTS

| | | |
|---|---|---|
| EP | 1687065 A2 | 8/2006 |
| WO | 1998021972 A2 | 5/1998 |
| WO | 2001028603 A1 | 4/2001 |
| WO | 2005053795 A2 | 6/2005 |

OTHER PUBLICATIONS

Speed et al., Sci. Rep., 2016, vol. 6, 26251.*
"The use of bone morphogenic proteins (BMPs) in long-bone non-unions," Current Orthopaedics, vol. 21, Issue 4, Aug. 2007, pp. 268-279. Abstract.

* cited by examiner

*Primary Examiner* — Xiaozhen Xie
(74) *Attorney, Agent, or Firm* — Sorell, Lenna & Schmidt LLP; William D. Schmidt, Esq.

(57) ABSTRACT

A method of treating a bone defect is provided. The method comprises administering to the bone defect an amount of about 0.1 μg to about 800 μg of growth differentiation factor 5 (GDF-5) over a period of at least three days. An implantable matrix for treating a bone defect is also provided.

7 Claims, 5 Drawing Sheets

SUSTAINED DELIVERY OF A GROWTH DIFFERENTIATION FACTOR

BACKGROUND

Bone defects may be caused by a number of different factors including trauma, pathological disease or surgical intervention. Because bone provides both stability and protection to an organism, these defects can be problematic. In order to address these defects, compositions and carriers that contain both natural and synthetic materials have been developed. These compositions and carriers may, depending upon the materials contained within them, be used to repair tissues and to impart desirable biological and/or mechanical properties to the bone defect.

Compositions and carriers may contain materials that are naturally found in mammalian bone tissue which contains one or more proteinaceous materials, active during growth and natural bone healing that can induce a developmental cascade of cellular events resulting in bone formation. Various developmental factors are present in bone. These factors include bone morphogenetic proteins (BMPs), other bone inductive proteins, bone growth factors, or osteogenic proteins.

A family that is in the superfamily of transforming growth factor-beta (TGF-β) and that is related to the BMP family is the growth differentiation factor (GDF) family. The GDF family provokes morphogenetic effects such as growth, differentiation, protection and regeneration of a variety of tissues and organs, such as bone, cartilage, tendons, ligaments, nerves and skin. One protein from the GDF family that has been recently used in the medical field is GDF-5. GDF-5 has been identified to be a very effective promoter of bone, cartilage and connective tissue formation. Further, the osteogenic properties of GDF-5 have been successfully used to aid in the healing of local bone fractures.

Therefore, it would be beneficial to provide methods and compositions to deliver sustained release of GDF-5 directly into a bone defect to expediate the healing process of the bone defect, such as a long-bone fracture. It would also be beneficial to provide an implantable matrix for treating a bone defect that releases an amount of the GDF-5 over a period of time.

SUMMARY

Methods, compositions and implants are provided for treating a bone defect with GDF-5. In some embodiments, a method of treating a bone defect is provided. The method comprises administering to the bone defect about 0.1 μg to about 800 μg of growth differentiation factor 5 (GDF-5) over a period of at least three days.

In some embodiments, a method of treating a bone defect is provided. The method comprises inserting an implantable medical device at, near or in the bone defect, the implantable medical device comprising growth differentiation factor 5 (GDF-5) and configured to release about 0.1 μg to about 800 μg of the GDF-5 over a period of at least three days.

In some embodiments, an implantable matrix for treating a bone defect is provided. The implantable matrix comprises a biodegradable polymer and growth differentiation factor 5 (GDF-5) disposed throughout the biodegradable polymer. The implantable matrix is configured to release about 0.1 μg to about 800 μg of the GDF-5 over a period of at least three days.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings.

Figure 1:
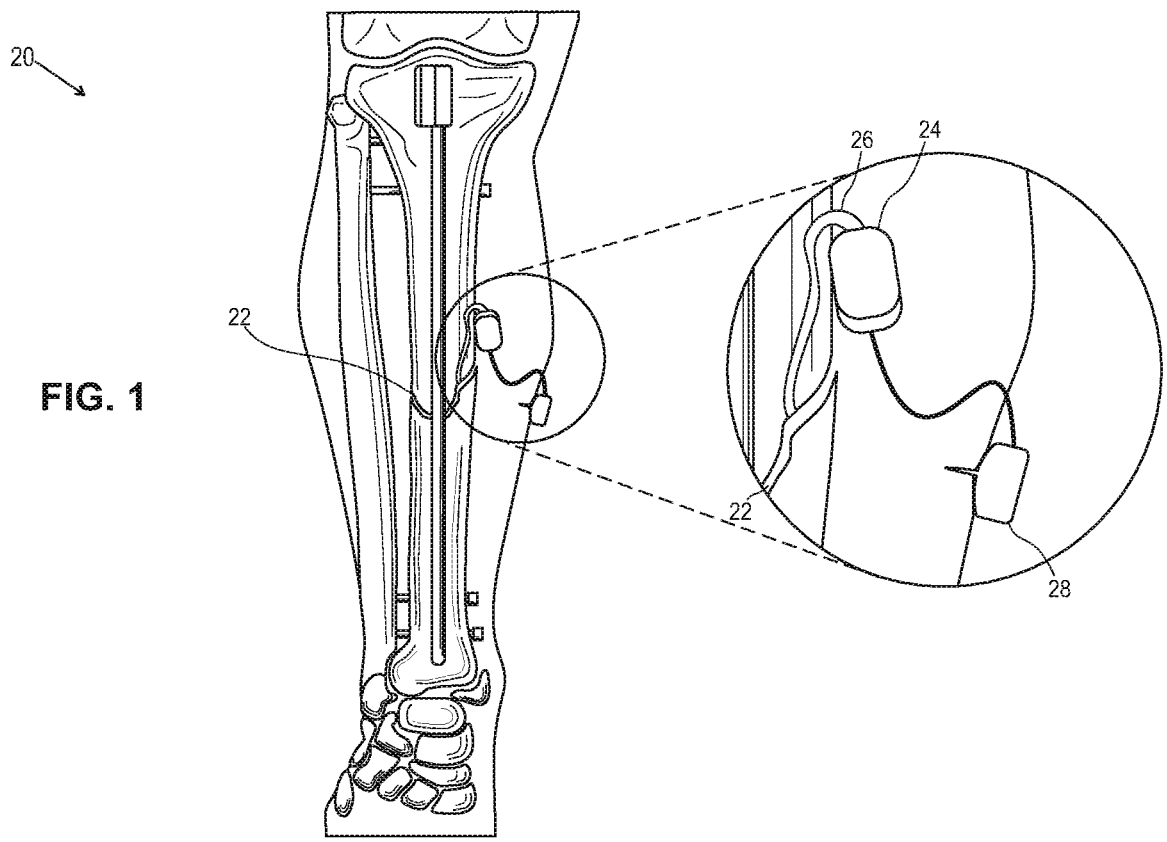
FIG. 1 is an illustration of an amount of GDF-5 being administered to a bone defect, such as a long bone fracture of a patient through an implantable pump. In this embodiment, the implantable pump is percutaneously implanted within the leg of the patient and a catheter attached to the pump is positioned at the bone defect to administer the GDF-5 to the bone defect.

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of promoting an understanding of the principles of the disclosure, reference will now be made to certain embodiments and specific language will be used to describe the same. It will nevertheless be understood that no limitation of the scope of the disclosure is thereby intended, such alterations and further modifications in the illustrated device, and such further applications of the principles of the disclosure as described herein being contemplated as would normally occur to one skilled in the art to which the disclosure relates.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations; the numerical representations are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this disclosure belongs.

Unless explicitly stated or apparent from context, the following terms are phrases have the definitions provided below.

Definitions

It is noted that, as used in this specification and the appended claims, the singular forms "a," "an," and "the," include plural referents unless expressly and unequivocally limited to one referent. Thus, for example, reference to "a dose" includes one, two, three or more doses.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "mammal" refers to organisms from the taxonomy class "mammalian," including but not limited to humans, other primates such as chimpanzees, apes, orangutans and monkeys, rats, mice, cats, dogs, cows, horses, etc.

A "therapeutically effective amount" or "effective amount" is such that when administered, the drug (e.g., growth factor) results in alteration of the biological activity, such as, for example, promotion of bone, cartilage and/or other tissue (e.g., vascular tissue) growth, reduction or alleviation of pain, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired.

The terms "treating" and "treatment" when used in connection with a disease or condition refer to executing a protocol that may include a bone repair procedure, where the bone implant and/or one or more drugs are administered to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention does not require complete alleviation of signs or symptoms, does not require a cure, and specifically includes protocols that have only a marginal effect on the patient.

The term "bone," as used herein, refers to bone that is cortical, cancellous or cortico-cancellous of autogenous, allogeneic, xenogeneic, or transgenic origin.

The term "osteoconductive," as used herein, refers to the ability of a non-osteoinductive substance to serve as a suitable template or substance along which bone may grow.

The term "osteoinductive," as used herein, refers to the quality of being able to recruit cells from the host that have the potential to stimulate new bone formation. Any material that can induce the formation of ectopic bone in the soft tissue of an animal is considered osteoinductive. Osteoinduction refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "parenteral," as used herein, refers to modes of administration which bypass the gastrointestinal tract, and include for example, intramuscular, intraperitoneal, intrasternal, subcutaneous, percutaneously, intra-operatively, intrathecally, intradiskally, peridiskally, epidurally, perispinally, intraarticular or combinations thereof.

The term "percutaneous," as used herein, refers to administration of a composition directly through the skin of the patient and into the bloodstream.

The term "osteoconduction" refers to the ability to stimulate the attachment, migration, and distribution of vascular and osteogenic cells within a matrix. The physical characteristics that affect the matrix's osteoconductive activity include porosity, pore size, and three-dimensional architecture. In addition, direct biochemical interactions between matrix proteins and cell surface receptors play a major role in the host's response to the matrix.

The term "osteogenic" refers to the ability of the injectable solution to produce bone independently. To have direct osteogenic activity, the injectable solution must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

"Resorbable", as used herein, refers to a matrix that exhibits chemical dissolution when placed in a mammalian body. The injectable bone morphogenetic protein does not need a stationary resorbable matrix. For example, the stationary matrix comprises an implant that is fixed in the body at the bone defect for a period of time. The matrix can be resorbable and/or non-resorbable for that period of time (e.g., 3 days to 6 months).

The term "solution" refers to a homogeneous liquid preparation that contains one or more chemical substances dissolved (e.g., molecularly dispersed), in a suitable solvent or mixture of mutually miscible solvents. Typically, solutions are mixtures with particle sizes of less than $10^{-7}$ cm. The aqueous carrier that is used to administer the GDF-5 can be a solution.

The term "suspension" refers to a two-phase system with uniform dispersion of finely divided solid particles in a continuous phase of liquid in which the particles have minimum solubility and a particle size greater than $10^{-5}$ cm. Here in suspensions, the finely divided solid particles are called as dispersed phase or external phase or discontinuous phase and the phase in which they are dispersed is called as dispersion medium or internal phase or continuous phase. The aqueous carrier that is used to administer the GDF-5 can be a suspension.

The term "biodegradable" includes that all or parts of the matrix that will degrade over time by the action of enzymes, by hydrolytic action and/or by other similar mechanisms in the human body to release the GDF-5. In various embodiments, "biodegradable" includes that the matrix can break down or degrade within the body to non-toxic components after or while a therapeutic agent (e.g., GDF-5) has been or is being released. By "bioerodible" it is meant that the matrix will erode or degrade over time due, at least in part, to contact with substances found in the surrounding tissue, fluids or by cellular action. By "bioabsorbable" it is meant that the matrix will be broken down and absorbed within the human body, for example, by a cell or tissue. "Biocompatible" means that the matrix will not cause substantial tissue irritation or necrosis at the target tissue site.

In some embodiments, the matrix has pores that allow release of the drug from the matrix. The matrix will allow fluid in the matrix to displace the drug. However, cell infiltration into the matrix will be prevented by the size of the pores of the matrix and the drug that is selected. In this way, in some embodiments, the matrix should not function as a tissue scaffold and allow tissue growth. Rather, the matrix will solely be utilized for drug delivery. In some embodiments, the pores in the matrix will be less than 250 to 500 microns. This pore size will prevent cells from infiltrating the matrix and laying down scaffolding cells. In some embodiments, this can be achieved by crosslinking. Thus, in this embodiment, drug will elute from the matrix as fluid enters the matrix, but cells will be prevented from entering. In some embodiments, where there are little or no pores, the drug will elute out from the matrix by the action of enzymes, by hydrolytic action and/or by other similar mechanisms in the human body.

In some embodiments, the biodegradable porous matrix has pores that are greater than 250 to 500 microns to allow certain types of cell to infiltrate the biodegradable porous matrix and lay down scaffolding cells (e.g., osteoclasts, osteoblasts, etc.).

The phrases "sustained release" and "sustain release" (also referred to as extended release or controlled release) are used herein to refer to the therapeutic agent(s) (e.g., GDF-5) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the matrix, or component thereof, or as the result of metabolic transformation or dissolution of the therapeutic agent(s) or conjugates of therapeutic agent(s).

The phrase "immediate release" is used herein to refer to the therapeutic agent(s) that is introduced into the body and that is allowed to dissolve in or become absorbed at the location to which it is administered, with no intention of delaying or prolonging the dissolution or absorption of the drug. For example, the therapeutic agent can be administered in a solution by single injection and this would be considered immediate release.

The two types of formulations (sustained release and immediate release) may be used in conjunction. The sustained release and immediate release may be in one or more of the same matrices. In various embodiments, the sustained release and immediate release may be part of separate matrices. For example, a bolus or immediate release formulation of a GDF-5 composition may be placed at or near the target site and a sustain release formulation may also be placed at or near the same site. Thus, even after the bolus becomes completely accessible, the sustained release formulation would continue to provide the therapeutic agent for the intended tissue.

In various embodiments, the matrix can be designed to cause an initial burst dose of therapeutic agent within the first twenty-four to forty-eight or seventy-two hours after implantation. "Initial burst" or "burst effect" or "bolus dose" refers to the release of therapeutic agent from the matrix during the first twenty-four hours to forty-eight or seventy-two hours after the matrix comes in contact with an aqueous fluid (e.g., synovial fluid, cerebral spinal fluid, etc.). The "burst effect" is believed to be due to the increased release of therapeutic agent from the matrix. In alternative embodiments, the matrix (e.g., gel) is designed to avoid or reduce this initial burst effect (e.g., by applying an outer polymer coating to the matrix). In some embodiments, the matrix has a burst release surface that releases about 5%, 10%, 15%, 20%, 25%, 30%, 35%, 45%, 50%, 55%, 60%, 65%, 70%, 75%, 80%, 85%, 90% to about 95% of the GDF-5 over 24 or 48 hours.

The term "implantable" as utilized herein refers to a biocompatible device (e.g., matrix) retaining potential for successful placement within a mammal. The expression "implantable device" and expressions of the like import as utilized herein refers to an object implantable through surgery, injection, or other suitable means whose primary function is achieved either through its physical presence or mechanical properties.

Reference will now be made in detail to certain embodiments of the disclosure. The disclosure is intended to cover all alternatives, modifications, and equivalents that may be included within the disclosure as defined by the appended claims.

The headings below are not meant to limit the disclosure in any way; embodiments under any one heading may be used in conjunction with embodiments under any other heading.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

Growth Differentiation Factor 5 (GDF-5)

GDF-5 is a member of the bone morphogenic protein family and plays roles in organ development processes including bone, cartilage, ligament, and joint formation. GDF-5 is involved in the formation of bone and cartilage. Similar to other members of BMPs, the signaling cascade of GDF-5 is originated through binding to type I and type II receptors and thus regulating the downstream intracellular biochemical processes. Human GDF-5 is recombinantly produced in *E coli*. It is produced as a homodimer, non-glycosylated polypeptide chain containing 2×117 amino acids with a molecular weight of 26.8 kDa. Human GDF-5 is available from Sigma-Aldrich St. Louis, Mo., USA. Suitable methods of making GDF-5 is described in U.S. Publication Nos. 2014/0213776, 2014/0212952, 2014/0212951 and 2014/0212924, which are hereby incorporated by reference in their entirety.

Methods, compositions and implants are provided for treating a bone defect with GDF-5. In some embodiments, a method of treating a bone defect is provided. The method comprises administering to the bone defect about 0.1 µg to about 800 µg of growth differentiation factor 5 (GDF-5) over a period of at least three days.

A method of treating a bone defect with GDF-5 is shown in 20, where a solution of GDF-5 is provided that is administered to a patient in order to create bone growth at the site of an injury such as a bone defect 22, as shown in FIG. 1. Illustrative target tissue sites (e.g., bone defect sites) that can be treated with the solution of the disclosure include, for instance, those resulting from injury, defects brought about during the course of surgery, infection, malignancy or developmental malformation. Specific bones which can be repaired or replaced with the bone material include, but are not limited to the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones. In some embodiments, the solution is administered percutaneously to a long bone fracture.

The solution comprises a therapeutically effective amount of GDF-5, in an amount of about 0.1 µg to about 800 µg in an aqueous carrier over a period of time of at least three days. In some embodiments, the GDF-5 can be administered at a dose in an amount of about 0.1 to about 1000 µg. In some embodiments, the GDF-5 can be administered in an amount from about 0.1, 0.05, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 to about 1000 µg.

In some embodiments, the GDF-5 is administered in an amount of about 20 µg to about 200 µg to fuse the bone defect. In some embodiments, the GDF-5 is administered in an amount of about 40 µg to about 100 µg to fuse the bone defect. It is to be understood that GDF-5 can be administered to a mammal, including, but not limited to a human or a rat.

In some embodiments, the GDF-5 can be administered over a period of time. In some embodiments, the GDF-5 can be administered over a period of 1 day to about three months. In some embodiments, the GDF-5 can be administered over a period of time from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 to about 90 days. In some embodiments, the GDF-5 can be administered to the site of injury, such as a bone defect by a continuous infusion.

In some embodiments, the GDF-5 can be administered in an aqueous solution or an aqueous carrier in an amount of about 1 to about 98% of the solution or carrier. In some embodiments, the GDF-5 is in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99% of the aqueous solution or carrier.

In some embodiments, the aqueous carrier is not osteoinductive or osteoconductive and is only used as a vehicle for delivery of the GDF-5. The aqueous carrier can include, but is not limited to saline, dextrose, sterile water for injection, phosphate buffered saline, blood, or a combination thereof. The aqueous carrier can be blood, for example, the patient's own blood and the blood can be combined with clotting factors.

Exemplary aqueous carriers include, but are not limited to, sterile water, bacteriostatic water for injection (BWFI), a pH buffered solution (e.g. phosphate-buffered saline), sterile saline solution, Ringer's solution or dextrose solution.

In some embodiments, the aqueous carrier can be in an amount of about 1, 2, 3, 4, 5, 6, 7, 8, 9 or 10 ml. For example, the aqueous solution can comprise 20 µg of GDF-5 in 1 ml of an aqueous carrier, 40 µg of GDF-5 in 2 ml of an aqueous carrier, 60 µg of GDF-5 in 3 ml of an aqueous carrier, 80 µg of GDF-5 in 1 ml of an aqueous carrier, 100 µg of GDF-5 in 2 ml of an aqueous carrier, 120 µg of GDF-5 in 3 ml of an aqueous carrier, 140 µg of GDF-5 in 1 ml of an aqueous carrier, 160 µg of GDF-5 in 2 ml of an aqueous carrier, or 180 µg of GDF-5 in 2 ml of an aqueous carrier or 200 µg of GDF-5 in 2 ml of an aqueous carrier.

In some embodiments, the aqueous carrier can be in an amount of about 1 to about 99.9% of the aqueous solution. In some embodiments, the aqueous carrier is in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 to about 99.9% of the aqueous solution.

In some embodiments, as shown in FIG. 1, the GDF-5 can be administered to the bone defect by an implantable pump 24. In some embodiments, the implantable pump is connected to a catheter 26 that administers the GDF-5 to the bone defect. In some embodiments, the pump can be attached to a port 28 located on the outside of the patient.

In some embodiments, the pump is an infusion pump that is an implantable controlled release device or sustained release delivery system that can release a certain amount of the GDF-5 per hour or in intermittent bolus doses. In some embodiments, the pump can be the SynchroMed® (Medtronic, Minneapolis, Minn.) pump. This pump has three sealed chambers. One contains an electronic module and battery. The second contains a peristaltic pump and drug or solution reservoir. The third contains an inert gas that provides the pressure needed to force the GDF-5 into the peristaltic pump. To fill the pump, the GDF-5 administered in the aqueous carrier is injected through the reservoir fill port to the expandable reservoir. The inert gas creates pressure on the reservoir, and the pressure forces the GDF-5 through a filter and into the pump chamber. The GDF-5 is then pumped out of the device from the pump chamber and into the catheter, which will direct it for deposit at the bone defect. The rate of delivery of GDF-5 is controlled by a microprocessor. This allows the pump to be used to deliver similar or different amounts of GDF-5 continuously, continually, at specific times, or at set intervals between deliveries. The SynchroMed® pump allows continuous infusion of the GDF-5 and mimics the release from a sustained release matrix (e.g., a collagen matrix).

In some embodiments, the implantable pump can be an Alzet® pump (Alzet Osmotic Pumps, Cupertino, Calif.). An Alzet® pump can be used for systemic administration when implanted subcutaneously or intraperitoneally. The pump can be attached to a catheter for intravenous, intracerebral, or intra-arterial infusion. An Alzet® pump can also be used for targeted delivery, where the effects of a drug or test agent are localized in a particular tissue or organ, by means of a catheter. The Alzet® pump allows continuous infusion of the GDF-5 and mimics the release from a sustained release matrix (e.g., a collagen matrix).

In some embodiments, the aqueous carrier can include a buffering agent, including, but not limited to, tris(hydroxymethyl)aminomethane (Tris), ethylenediaminetetraacetic acid (EDTA), (2-[4-(2-hydroxyethyl)-1-piperazinyl]ethanesulfonic acid) (HEPES), sodium acetate, sodium citrate, sodium phosphate, 2-(N-morpholino)ethanesulfonic acid (MES), phosphate buffered saline (PBS), sodium phosphate, potassium phosphate, sodium chloride, potassium chloride, glycerol, calcium chloride, sucrose, glycine, L-glutamic acid, polysorbate 80 or a combination thereof. In some embodiments, the buffering agent is sucrose, glycine, L-glutamic acid, sodium chloride, polysorbate 80 or a combination thereof.

Additional buffering agents may include, but are not limited to, alkaline earth metal carbonates, phosphates, bicarbonates, citrates, borates, acetates, succinates, or others.

Illustrative-specific buffering agents include for instance sodium phosphate, sodium citrate, sodium borate, sodium acetate, sodium bicarbonate, and sodium carbonate.

In some embodiments, the buffering agent can be in the aqueous carrier at a concentration from about 1 mM to 100 mM. The buffering agent can be in the aqueous carrier at a concentration of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 mM.

In some embodiments, the aqueous carrier can have a pH of from about 3.0 to about 7.0, from about 4.0 to about 6.0 or from about 4.5 to about 5.5. It is contemplated that the pH of the aqueous carrier can be from about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9 to about 7.0.

Figure 2:
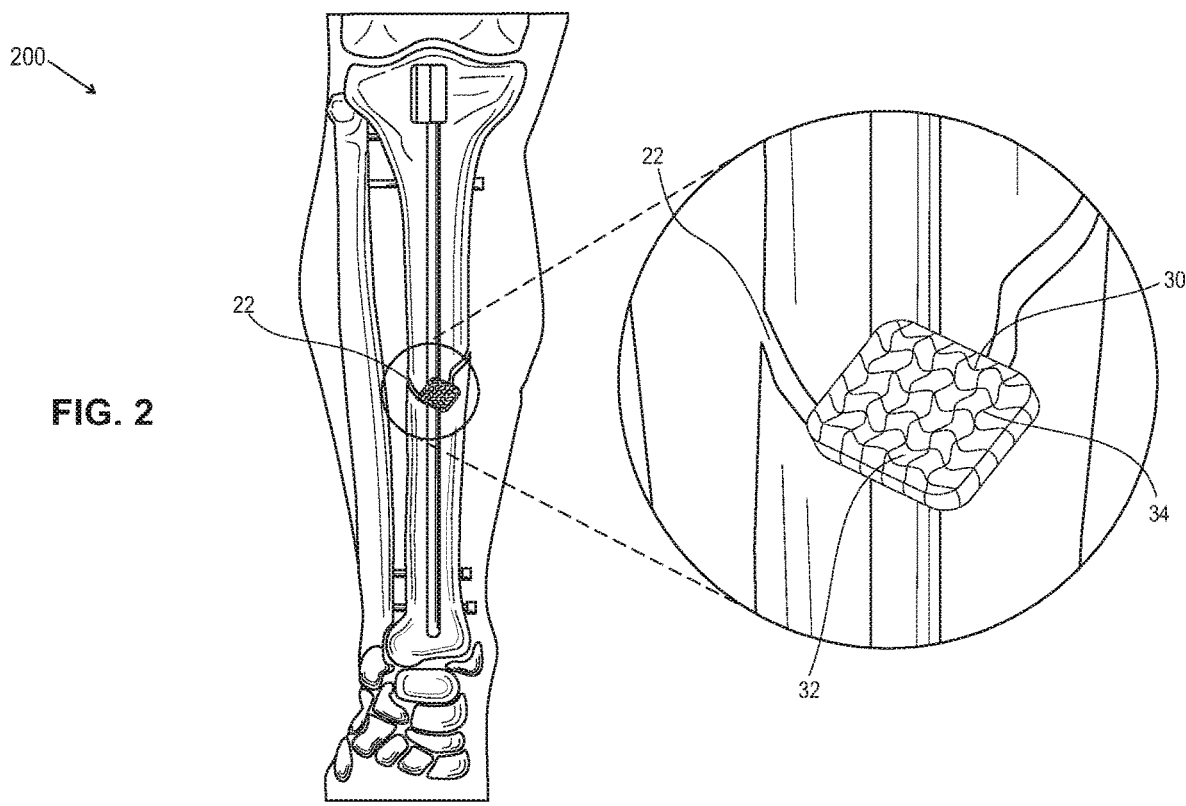
FIG. 2 is an illustration of an implantable matrix comprising a biodegradable polymer and GDF-5 for treating a bone defect. In this embodiment, the implantable matrix is percutaneously implanted within the leg of the patient at the bone defect to administer the GDF-5 via sustained release to the bone defect.

In some embodiments, as shown in FIG. 2, a method of treatment is shown 200 where the GDF-5 can be administered to a bone defect 22 by an implantable medical device such as an implantable matrix 30. The implantable matrix can be inserted at, near, or in the bone defect to treat the bone defect. The implantable matrix comprises a biodegradable polymer 32 and the GDF-5. The GDF-5 is disposed throughout the biodegradable polymer. The implantable matrix is configured to release about 0.1 µg to about 800 µg of the GDF-5 over a period of at least three days.

In some embodiments, the implantable matrix can release an amount of GDF-5 from about 0.1, 0.05, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 to about 1000 µg.

In some embodiments, the implantable matrix can release GDF-5 in an amount of about 20 µg to about 200 µg to fuse the bone defect. In some embodiments, the implantable matrix can release GDF-5 in an amount of about 40 µg to about 100 µg to fuse the bone defect.

In some embodiments, the GDF-5 can be released from the implantable matrix over a period of time, such as, for example, over a period of at least three days. In some embodiments, the implantable matrix releases the GDF-5 over a period of about one week to about six months to grow bone. In some embodiments, the implantable matrix releases the GDF-5 over a period of time from about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179 to about 180 days.

In some embodiments, the implantable matrix comprises a surface 34 that releases a burst dose of the GDF-5 in an amount from about 5% to about 20% by weight based on the total weight of GDF-5 in the matrix within 24 hours. In some embodiments, the surface of the implantable matrix releases a burst dose of GDF-5 in an amount from about 5, 6, 7, 8, 9, 10, 11, 12, 13, 14, 15, 16, 17, 18, 19 to about 20% by weight based on the total weight of GDF-5 in the matrix within 24 hours.

In some embodiments, the implantable matrix comprises GDF-5 in an amount of from about 5 wt. % to about 90 wt. % based on the weight of the matrix. In other embodiments, the implantable matrix comprises GDF-5 in an amount from about 10 wt. % to about 80 wt. %, from about 20 wt. % to about 70 wt. %, from about 30 wt. % to about 60 wt. %, or from about 40 wt. % to about 50 wt. % based on the weight of the implantable matrix. In some embodiments, the loading of the GDF-5 is from about 0.25, 0.5, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 to about 90 wt. % based on the weight of the implantable matrix.

In some embodiments, there is a higher loading of GDF-5, e.g., at least 20, at least 30, at least 40, at least 50, at least 60, at least 70, at least 80, or at least 90% of GDF-5 disposed in the implantable matrix.

In some embodiments, the biodegradable polymer may comprise natural and/or synthetic material(s). For example, the biodegradable may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, PEAs, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In some embodiments, the implantable matrix comprises collagen. The starting material for producing collagen can be purified collagen, native collagen or modified collagen of any type. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the implantable matrix comprises a collagen that is in the implantable matrix in an amount of from about 0.25%, 0.5%, 0.75%, 1 wt. %, 2 wt. %, 3 wt. %, 4 wt. %, 5 wt. %, 10%, 15%, 200/%, 25%, 30%, 35%, 45%, 50%, 55%, 600a, 65%, 70%, 75%, 80%, 85%, 90%, to about 99 wt. % by weight of the implantable matrix.

In some embodiments, the implantable matrix comprises polysaccharides, including, but not be limited to hyaluronic acid, chondroitin sulfate, dermatan sulfate, keratan sulfate, heparan, heparan sulfate, dextran, dextran sulfate, alginate, and other long chain polysaccharides. Typically, the polysaccharide can have an average molecular weight of about 1,000 to 10,000,000 DA. Hyaluronic acid is a natural component of the cartilage extracellular matrix, and it is readily sterilized, is biodegradable and can be produced in a wide range of consistencies and formats. It is generally biocompatible and its resorption characteristics can be controlled by the manipulation of monomers to polymer forms, most commonly through the esterification of the carboxylic groups of the glucuronic acid residues.

In some embodiments, the implantable matrix comprises the biodegradable polymer in an amount of from about 5 wt. % to about 90 wt. % based on the weight of the matrix. In other embodiments, the implantable matrix comprises the biodegradable polymer in an amount from about 10 wt. % to about 80 wt. %, from about 20 wt. % to about 70 wt. %, from about 30 wt. % to about 60 wt. %, or from about 40 wt. % to about 50 wt. % based on the weight of the implantable matrix. In some embodiments, the implantable matrix comprises the biodegradable polymer in an amount from about 0.25, 0.5, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 to about 90 wt. % based on the weight of the implantable matrix.

In some embodiments, the implantable matrix can be porous. In some embodiments, the implantable matrix comprises a plurality of pores. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, the implantable matrix has a porosity of at least about 30%, at least about 50%, at least about 60%, at least about 70%, at least about 90%. The pores enhance release of the GDF-5 and may support ingrowth of cells, formation or remodeling of bone, cartilage and/or vascular tissue after release of most of the GDF-5.

In some embodiments, the GDF-5 can be disposed in discrete regions of the implantable matrix, can be disposed uniformly into the implantable matrix or can be layered into the implantable matrix. In some embodiments, the implantable matrix can comprise fibers having the GDF-5 disposed within the fibers (e.g., electrospun GDF-5 fibers). The fibers may, in some embodiments, have a diameter ranging from 0.75 microns to 3 microns.

In some embodiments, the implantable matrix has a density of between about 1.6 g/cm$^3$, and about 0.05 g/cm$^3$. In some embodiments, the implantable matrix has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

In some embodiments, the shape of the implantable matrix may be tailored to the injury site at which it is to be situated. For example, it may be in the shape of a morsel, a plug, a pin, a peg, a cylinder, a block, a wedge, or a sheet.

In some embodiments, the implantable matrix may comprise a resorbable ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof.

In some embodiments, the implantable matrix may contain an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, by including inorganic ceramics, such as for example, calcium phosphate, in the implantable matrix, this will act as a local source of calcium and phosphate to the cells attempting to deposit new bone. The inorganic ceramic also provides compression resistance and load bearing characteristics to the implantable matrix.

In some embodiments, the implantable matrix comprises the ceramic particles in an amount from about 30 wt % to about 99.5 wt % of the implantable matrix. In some embodiments, the implantable matrix comprises from about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to about 99.5 wt % by weight of ceramic particles in the implantable matrix.

In some embodiments, the mineral particles in the implantable matrix comprise tricalcium phosphate and hydroxyapatite in a ratio of about 80:20 to about 90:10. In some embodiments, the mineral particles in the implantable matrix comprise tricalcium phosphate and hydroxyapatite in a ratio of about 70:30 to about 95:5. In some embodiments, the mineral particles in the implantable matrix comprise tricalcium phosphate and hydroxyapatite in a ratio of about 85:15.

In some embodiments, the implantable matrix can contain demineralized bone material disposed therein. The demineralized bone material can include demineralized bone, powder, chips, triangular prisms, spheres, cubes, cylinders, shards, fibers or other shapes having irregular or random geometries. These can include, for example, "substantially demineralized," "partially demineralized," or "fully demineralized" cortical and cancellous bone. These also include surface demineralization, where the surface of the bone construct is substantially demineralized, partially demineralized, or fully demineralized, yet the body of the bone construct is fully mineralized. The configuration of the bone material can be obtained by milling, shaving, cutting or machining whole bone as described in for example U.S. Pat. No. 5,899,939. The entire disclosure is herein incorporated by reference into the present disclosure.

In some embodiments, the implantable matrix may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

In some embodiments, the GDF-5 may be disposed on or in the implantable matrix by hand by soaking, electro spraying, ionization spraying or impregnating, vibratory dispersion (including sonication), nozzle spraying, compressed-air-assisted spraying, brushing and/or pouring.

In some embodiments, initial burst surfaces can be disposed on the edges of the implantable matrix so that upon contact with the bone defect, the edges will begin to release the GDF-5. In some embodiments, the implantable matrix can include a core of dense, entangled polymers and can contain the GDF-5 to provide slower release of the GDF-5.

In various embodiments, the ratio of free to bound GDF-5 disposed within the implantable matrix is about 90:10, 80:20, 70:30, 60:40, 50:50, 40:60, 30:70, 20:80 and 10:90. In some embodiments, the ratio of free to bound GDF-5 is dependent on the manner in which GDF-5 is distributed within the implantable matrix, the degree of crosslinking performed, the amount of GDF-5 added to the implantable matrix and/or the amount of time that has elapsed. As bodily fluid contacts the matrix, GDF-5 is released (also referred to as free GDF-5) and some remains in or on the implantable matrix and is also referred to as bound GDF-5.

In some embodiments, the implantable matrix can have a modulus of elasticity in the range of about $1\times10^2$ to about $6\times10^5$ dynes/cm$^2$, or $2\times10^4$ to about $5\times10^5$ dynes/cm$^2$, or $5\times10^4$ dynes/cm$^2$ to about $5\times10^5$ dynes/cm$^2$.

In some embodiments, the implantable matrix may comprise a biodegradable polymer having a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the implantable matrix may have a burst release surface that releases about 100/%, 15%, 20%, 25%, 30%, 35%, 45%, 50, 55%, 60%, 65%, 70%, 75%, 80%, 85%, 90%, 95%, 96%, 97%, 98%, to 99% of the GDF-5 over 24 or 48 hours.

Expandable Phase

In some embodiments, the implant may comprise a material, such as, for example, an expandable phase, to facilitate swelling of the implant. The expandable phase comprises one or more polymers that swell upon taking in fluid (e.g., saline, water, bodily fluid, etc.), and thus increase the volume of the implant and which further holds the implant in position over time.

In some embodiments, the expandable phase comprises a range of about 0.1% to about 20% based on the total weight of the matrix or the implant. In some embodiments, the biodegradable polymer comprises a range of about 0.1% to about 10% based on the total weight of the matrix or the implant. In some embodiments, the expandable phase comprises 0.1%, 0.25%, 0.5%, 0.75%, 1%, 2%, 3%, 4%, 5%, 6%, 7%, 8%, 9% or 10% based on the total weight of the matrix or the implant.

In some embodiments, the expandable phase comprises polymers, monomers, starches, gums, poly(amino acids) or a combination thereof that swell upon contact with fluid (water, saline, body fluids, etc.). In various embodiments, the amount of swelling can range from 5 to 100 percent, 5 to 40 percent, or 5 to 20 percent. The time to reach maximum swelling can be varied depending on the location and desired property of the implant. In some embodiments, the time to reach maximum swelling can occur within a period of 5 days, 3 days, 2 days or within a period of 24 hours.

Suitable swellable material may include, for example, hydroxypropyl cellulose, hydroxypropyl methylcellulose, hydroxyethyl methylcellulose, carboxymethylcellulose, hydroxyethylcellulose and salts thereof, Carbopol, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, PEG 200, PEG 300, PEG 400, PEG 500, PEG 550, PEG 600, PEG 700, PEG 800, PEG 900, PEG 1000, PEG 1450, PEG 3350, PEG 4500, PEG 8000 or combinations thereof. In some embodiments, the expandable phase includes gelling polymers including but not limited to cellulosic polymers, vinyl polymers, such as polyvinylpyrrolidone; acrylic polymers and copolymers, such as acrylic acid polymer, methacrylic acid copolymers, ethyl acrylate-methyl methacrylate copolymers, or the like; or mixtures thereof.

A non-limiting list of swellable materials which the expandable phase may comprise include polyvinyl alcohol (PVA), PVA modified with hydrophilic co-monomers, e.g., AMPS, PVA modified with fast crosslinking groups, e.g., NAAADA, PVA modified with polyvinylpyrroline (PVP), carboxymethylcellulose, polyethylene glycol (PEG), poly (vinyl ether), co-polymers of PVA and PEG, polypropylene glycol (PPG), co-polymers of PEG and PPG, co-polymers of PVA or PPG, polyacrylonitrile, hydrocolloids, e.g. agar, alginates, collagen, elastin, chitin, chitosan, gelatin, sugar, mannitol, or the like. In various embodiments, the swellable material includes, for example, poly(N-isopropylacrylamide-co-acrylic acid)-poly(L-lactic acid) (NAL); poly(N-isopropyl acrylamide) (PNIPAM) grafted to other polymers such as carboxymethylcellulose (CMC) copolymers or polymers including block copolymers and end-functionalized polymers, composites or copolymers containing thermosensitive poly(2-ethoxyethyl vinyl ether) and/or poly(hydroxyethyl vinyl ether) and/or (EOVE200-HOVE400).

The swellable material, in various embodiments, may be used to control release of the GDF-5 into the bone tissue.

In some embodiments, the expandable phase includes hyaluronic acid. In some embodiments, the expandable phase includes glycosaminoglycans. Non-limiting examples of glycosaminoglycans include chondroitin sulfate, dermatan sulfate, keratin sulfate, heparin, heparan sulfate, and hyaluronan. In some embodiments, the expandable phase includes mannitol, PEG, magnesium alginate or glycerol.

The polymers may be crosslinked, are not crosslinked, or are lightly crosslinked hydrophilic polymers. Although these polymers may be non-ionic, cationic, zwitterionic, or anionic, in various embodiments, the swellable polymers are cationic or anionic. In various embodiments, the swellable polymer may contain a multiplicity of acid functional groups, such as carboxylic acid groups, or salts thereof. Examples of such polymers suitable for use herein include those which are prepared from polymerizable, acid-containing monomers, or monomers containing functional groups which can be converted to acid groups after polymerization. Examples of such polymers also include polysaccharide-based polymers such as carboxymethyl starch and cellulose, and poly(amino acid) polymers such as poly(aspartic acid). Some non-acid monomers may also be included, usually in minor amounts, in preparing the absorbent polymers.

Such non-acid monomers include, for example, monomers containing the following types of functional groups: carboxylate or sulfonate esters, hydroxyl groups, amide groups, amino groups, nitrile groups, quaternary ammonium salt groups, and aryl groups (e.g. phenyl groups, such as those derived from styrene monomer). Other potential non-acid monomers include unsaturated hydrocarbons such as ethylene, propylene, I-butene, butadiene, or isoprene.

In some embodiments, the expandable phase comprises substances which are capable of becoming freely permeable following hydration in aqueous fluids. Such substances include polysaccharides, such as gelatin, saccharose, sorbitol, mannanes, jaluronic acid, polyaminoacids, polyalcohols, polyglycols, or the like. In addition to the foregoing, the swellable polymer may also include additional excipients such as lubricants, flow promoting agents, plasticizers, and anti-sticking agents. For example, the expandable phase may further include polyethylene glycol, polyvinylpyrrolidone, talc, magnesium stearate, glyceryl behenate, stearic acid, or titanium dioxide.

In various embodiments, the particle size distribution of the expandable phase material may be about 10 micrometers, 13 micrometers, 85 micrometers, 100 micrometers, 151 micrometers, 200 micrometers and all subranges therebetween. In some embodiments, at least 75% of the particles have a size from about 10 micrometers to about 200 micrometers. In some embodiments, at least 85% of the particles have a size from about 10 micrometers to about 200 micrometers. In some embodiments, at least 95% of the particles have a size from about 10 micrometers to about 200 micrometers. In some embodiments, all of the particles have a size from about 10 micrometers to about 200 micrometers. In some embodiments, at least 75% of the particles have a size from about 20 micrometers to about 180 micrometers. In some embodiments, at least 85% of the particles have a size from about 20 micrometers to about 180 micrometers. In some embodiments, at least 95% of the particles have a size from about 20 micrometers to about 180 micrometers. In some embodiments, all of the particles have a size from about 20 micrometers to about 180 micrometers.

In some embodiments, a contemplated embodiment of the implantable matrix consists of, consists essentially of, or comprises optionally porous ceramic particles in an amount of about 30 wt % to about 99.5 wt % based on a total weight of the implantable matrix in a biodegradable polymer in an amount of about 0.1 wt % to about 20 wt % based on the total weight of the implantable matrix, and GDF-5 disposed in or on the implantable matrix. The implantable matrix can be compression resistant.

In some embodiments, a contemplated embodiment of the implantable matrix consists of, consists essentially of, or comprises GDF-5 in an amount from about 0.1 to about 5 wt %, collagen in an amount from about 5 wt % to about 15 wt %, optionally carboxymethyl cellulose (CMC) in an amount from about 1 wt % to about 5 wt % and optionally ceramic in an amount from about 50 wt % to about 80 wt %.

Additives

The aqueous carrier and/or the implantable matrix can further comprise additives such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. In some embodiments, the aqueous carrier and/or the implantable matrix may comprise sterile and/or preservative free material. These additives may have multi-functional purposes including the carrying and stabilizing of the BMP. The additives as described above, can be in an amount of about 0.001 to about 5 wt. % of the injectable solution. The additives can be in an amount of about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 1, 2, 3, 4 or 5% of the injectable solution.

The aqueous carrier and/or the implantable matrix can include clotting factors, including, but not limited to fibrinogen, prothrombin, tissue thromboplastin (tissue factor), ionized calcium (Ca++), labile factor or proaccelerin, stable factor or proconvertin, antihemophilic factor, plasma thromboplastin component, Christmas factor, Stuart-Prower factor, plasma thromboplastin antecedent, Hageman factor or fibrin-stabilizing factor. The clotting factors may be added to the injectable composition in an amount of about 0.0001% to about 5% of the injectable solution. The clotting factor or factors can be in an amount of about 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 1, 2, 3, 4 or 5%° of the injectable solution.

In some embodiments, the aqueous carrier and/or aqueous solution is free from a matrix material particularly a stationary matrix material. The term "free from a matrix," as used herein, refers to the injectable solution of the present disclosure not being disposed in a solid matrix or semi-solid matrix. Thus, the GDF-5 in the aqueous carrier and/or the aqueous solution is more than 95% to 99.9% to 100% free from matrices including, but not limited to, hydroxyethyl cellulose, hydroxypropyl cellulose, hydroxyethylmethyl cellulose, hydroxypropylmethyl cellulose, poly (alpha-hydroxy acids), poly (lactide-co-glycolide) (PLGA or PLG), polylactide (PLA), polyglycolide (PG), conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, caprolactone, dextrans, vinylpyrrolidone, PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, or combinations thereof.

In some embodiments, the aqueous carrier and/or the aqueous solution is a colorless solution and a coloring agent can be added to the colorless solution so that the user can now see the application to the target tissue site. In some embodiments, the mixture of the aqueous carrier and/or the aqueous solution and coloring agent is administered into the bone defect and then the user can view its distribution within the bone defect.

The aqueous carrier and/or the aqueous solution may have a molecular weight of from about 500 to about 30,000 Daltons (Da). In various embodiments, the aqueous carrier and/or the aqueous solution may have a molecular weight of from about 1,000 to about 10,000 Da. In some embodiments, the aqueous carrier and/or the aqueous solution may have a molecular weight of from about 2,000 to 4,000 Da or from about 3,000 to 4,000 Da. In some embodiments, the aqueous carrier and/or the aqueous solution may have a molecular weight of 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or about 30,000 Da.

In some embodiments, the aqueous carrier and/or the aqueous solution may or may not also contain other beneficial substances including for example preservatives, cosolvents, suspending agents, viscosity enhancing agents, ionic strength and osmolality adjusters and/or other excipients.

One or more additional biologically active ingredients may or may not be added to the resulting implantable matrix, aqueous carrier and/or the aqueous solution. These active ingredients may or may not be related to the bone repair capabilities of the implantable matrix, aqueous carrier and/or the aqueous solution. Suitable active ingredients are hemostatic agents, genes, growth differentiation factors (GDFs), or other non-collagenic proteins such as PDGF, ostropontin, osteonectin, cytokines, and the like.

In another embodiment, one or more additional GDFs may or may not be added either into the implantable matrix, aqueous carrier and/or the aqueous solution or administered to the bone defect site before administration of the injectable solution. Additional GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same. GDF-7 polynucleotides or polypeptides corresponding to GenBank Accession Numbers AB 158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP004855, as well as mature GDF-15 polypeptides or polynucleotides encoding the same.

In some embodiments, the implantable matrix, aqueous carrier and/or the aqueous solution contains other bioactive agents or these bioactive agents can be administered to the target tissue site prior to the implantable matrix, aqueous carrier and/or the aqueous solution being administered. In certain embodiments, the bioactive agent is a drug. These bioactive agents may include, for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergic, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, antiarthritics, and diagnostic agents.

A more complete listing of bioactive agents and specific drugs suitable for use in the present disclosure may be found in "The Merck Index: An Encyclopedia of Chemicals, Drugs, and Biologicals," Edited by Susan Budavari, et al.; and the United States Pharmacopoeia/National Formulary XXXVII/XXXII, published by the United States Pharmacopeial Convention, Inc., Rockville, Md., 2013, each of which is incorporated herein by reference.

Bioactive agents may also be provided by incorporation into the implantable matrix, aqueous carrier and/or the aqueous solution or can be administered before or after the implantable matrix, aqueous carrier and/or the aqueous solution is administered. Bioactive agents such as those described herein can be incorporated homogeneously into the implantable matrix, aqueous carrier and/or the aqueous solution by simple admixture or otherwise. Further, they may be incorporated alone or in conjunction with another carrier form or medium such as microspheres or another microparticulate formulation. Suitable techniques for forming microparticles are well known in the art and can be used to entrain or encapsulate bioactive agents, whereafter the microparticles can be dispersed within the bone material upon or after its preparation.

It will be appreciated that the amount of additive used will vary depending upon the type of additive, the specific activity of the particular additive preparation employed, and the intended use of the injectable solution. The desired amount is readily determinable by the user.

Any of a variety of medically and/or surgically useful substances can be incorporated in, or associated with, the injectable solution either before, during, or after preparation of the implantable matrix, aqueous carrier and/or the aqueous solution.

Lyophilization

In some embodiments, the GDF-5 is freeze-dried or is in a lyophilized form. Typically, in the freeze-dried or lyophilized form, an effective amount (e.g., 0.1 µg to about 800 µg) of the GDF-5 is provided. Lyophilized forms can be reconstituted into solutions, suspensions, emulsions, or any other suitable form for administration or use. Lyophilized GDF-5 is typically first prepared as liquids, then frozen and lyophilized. The total liquid volume before lyophilization can be less, equal to, or more than, the final reconstituted volume of the lyophilized GDF-5. The lyophilization process is well known to those of ordinary skill in the art, and typically includes sublimation of water from a frozen formulation under controlled conditions.

Lyophilized formulations can be stored at a wide range of temperatures. Lyophilized GDF-5 may be stored at or below 30° C., for example, refrigerated at 4° C., or at room temperature (e.g., approximately 25° C.).

Lyophilized GDF-5 are typically reconstituted for use by addition of an aqueous solution to dissolve the lyophilized GDF-5. A wide variety of aqueous solutions can be used to reconstitute lyophilized GDF-5. In some embodiments, lyophilized GDF-5 are reconstituted using water. In some embodiments, lyophilized GDF-5 can be reconstituted with a solution containing water (e.g., USP WFI, or water for injection) or bacteriostatic water (e.g., USP WFI with 0.9% benzyl alcohol). However, solutions comprising buffers and/or excipients and/or one or more pharmaceutically acceptable carriers can also be used. In some embodiments, the solutions do not contain any preservatives (e.g., are preservative free).

In some embodiments, the lyophilized GDF-5 can be disposed in a vial by the manufacturer and then the surgeon can mix the aqueous carrier with the lyophilized GDF-5 and/or with a diluent. This mixture can then be parenterally administered to the target tissue site. Aqueous carriers include, but are not limited to water, e.g., sterile water, solutions containing inorganic salts, or cationic surface-active agents including sodium chloride, saline, e.g., phosphate buffered saline, potassium chloride, sodium sulfate, potassium sulfate, EDTA, ammonium sulfate, ammonium acetate, and sodium acetate. Mixtures of two or more aqueous carriers can be used. The aqueous carriers can further include, for example, bone marrow aspirate, platelet concentrate, blood, pharmaceutical additives in solution, or combinations of these materials. Exemplary aqueous carriers include, but are not limited to, sterile water, bacteriostatic water for injection (BWFI), a pH buffered solution (e.g.

phosphate-buffered saline), sterile saline solution, Ringer's solution or dextrose solution. These can be used to reconstitute the BMP and dilute it for administration to the patient.

Methods of Treatment

As described above, illustrative bone defects that can be treated with the GDF-5 of the disclosure include, for instance, those resulting from injury, defects brought about during the course of surgery, infection, malignancy or developmental malformation. The GDF-5 can be used in a wide variety of orthopedic, periodontal, neurosurgical and oral and maxillofacial surgical procedures including, but not limited to the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the GDF-5, but are not limited to the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

In accordance with certain aspects of the disclosure, the GDF-5 administered in an aqueous carrier of the disclosure can be used in, on or around load bearing implants such as spinal implants, hip implants (e.g. in or around implant stems and/or behind acetabular cups), knee implants (e.g. in or around stems). In some embodiments, the GDF-5 administered in an aqueous carrier of the disclosure can be incorporated in, on or around a load-bearing spinal implant device having a compressive strength of at least about 10000 N, such as a fusion cage, PEEK implants, dowel, or other device potentially having a pocket, chamber or other cavity for containing an osteoinductive composition, and used in a spinal fusion such as an interbody fusion. One illustrative such use is in conjunction with a load-bearing interbody spinal spacer to achieve interbody fusion. In these applications, the GDF-5 loaded in an aqueous carrier can be placed in and/or around the spacer to facilitate the fusion.

In some embodiments, a method of treating a bone defect is provided, the method comprising administering to the bone defect about 0.1 µg to about 800 µg of growth differentiation factor 5 (GDF-5) over a period of at least three days.

In some embodiments, the GDF-5 is administered to the bone defect by a continuous infusion. In some embodiments, the GDF-5 is administered by an implantable pump. In some embodiments, the GDF-5 is administered in an aqueous carrier. In some embodiments, the aqueous carrier comprises saline, dextrose, sterile water for injection, phosphate buffered saline, blood, or a combination thereof.

In some embodiments, the GDF-5 is administered in an amount of about 20 µg to about 200 µg to fuse the bone defect. In some embodiments, the GDF-5 is administered in an amount of about 40 µg to about 100 µg to fuse the bone defect.

In some embodiments, the aqueous carrier further comprises a buffering agent comprising tris(hydroxymethyl) aminomethane (Tris), ethylenediaminetetraacetic acid (EDTA), (2-[4-(2-hydroxyethyl)-1-piperazinyl]ethanesulfonic acid) (HEPES), sodium acetate, sodium citrate, sodium phosphate, 2-(N-morpholino)ethanesulfonic acid (MES), phosphate buffered saline (PBS), sodium phosphate, potassium phosphate, sodium chloride, potassium chloride, glycerol, calcium chloride, sucrose, glycine, L-glutamic acid, polysorbate 80 or a combination thereof. In some embodiments, the buffering agent comprises sucrose, glycine, L-glutamic acid, sodium chloride, polysorbate 80 or a combination thereof.

In some embodiments, the buffering agent is in an aqueous carrier at a concentration from about 1 mM to 100 mM, and the aqueous carrier has a pH of from about 4.0 to about 6.0.

In some embodiments, a method of treating a bone defect is provided. The method comprises inserting an implantable medical device at, near or in the bone defect, the implantable medical device comprising growth differentiation factor 5 (GDF-5) and configured to release about 0.1 µg to about 800 µg of the GDF-5 over a period of at least three days. In some embodiments, the bone defect is a fracture.

In some embodiments, the implantable medical device releases the GDF-5 over a period of 1 week to 6 months to grow bone. In some embodiments, the GDF-5 is released in an amount of about 20 µg to about 200 µg to fuse the bone defect. In some embodiments, the implantable medical device comprises an implantable pump loaded with the GDF-5.

Kits

In various embodiments, a kit can be provided containing the GDF-5 administered in the aqueous carrier and/or the implantable matrix. In some embodiments, the kit may include additional parts along with the GDF-5 such as the aqueous carrier stored in a vial, the implantable matrix, the implantable pump, catheter, medical tools and/or vials containing buffering agents. The kit may include the GDF-5 in a first compartment. The GDF-5 can be in a dry, lyophilized form. The second compartment may include the aqueous carrier sealed in a vial or container, along with a vial containing a buffering agent and any other delivery instruments needed for the delivery. A third compartment may include the pump and catheter. A fourth compartment may contain gloves, drapes, wound dressings and other procedural supplies for maintaining sterility of the implanting process, as well as an instruction booklet, which may include a chart that shows how to implant the GDF-5. A fifth compartment may include additional needles, fasteners, and/or sutures.

Alternatively, the kit may include the implantable matrix loaded with the GDF-5 in a first compartment, a second compartment may contain gloves, drapes, wound dressings and other procedural supplies for maintaining sterility of the implanting process, as well as an instruction booklet, which may include a chart that shows how to implant the implantable matrix. A third compartment may include additional needles, fasteners, and/or sutures. Each tool may be separately packaged in a plastic pouch that is radiation sterilized. An additional compartment may include an agent for radiographic imaging. A cover of the kit may include illustrations of the implanting procedure and a clear plastic cover may be placed over the compartments to maintain sterility.

Having now generally described the invention, the same may be more readily understood through the following reference to the following examples, which are provided by way of illustration and are not intended to limit the present invention unless specified.

Examples

The experiments below demonstrate that a sustained release of GDF-5 administered to a bone defect through an implantable pump may be a viable treatment to augment fracture healing. The results also suggest that a single injection of GDF-5 does not work as effectively as sustained release of GDF-5. The implantable pump is a continuous infusion of GDF-5 and mimics the release of GDF-5 from a sustained release implantable and biodegradable polymer matrix.

Figure 4:
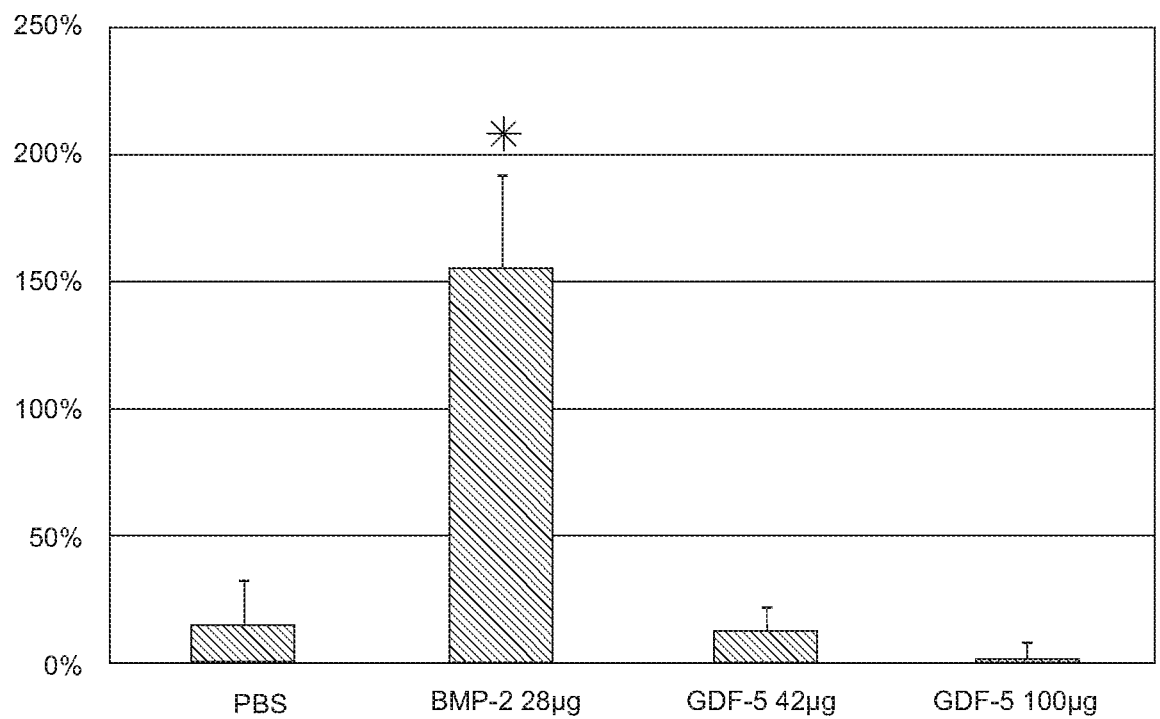
FIG. 4 is a graph depicting the percentage increase in maximal load at a bone defect (e.g., bone fracture) when 28 μg of BMP-2, 42 μg of GDF-5, and 100 μg of GDF-5 is administered to the bone compared to a non-treated control where Phosphate Buffered Saline (PBS) is administered to the bone. More particularly, a rat femoral fracture model was used to test the efficacy of a single injection of BMP-2 and GDF-5. Each solution was injected directly into the fracture site at the time of injury. Maximal load was applied to the bone and used as an outcome measure of bone strength and fracture healing.

As shown in FIG. 4, a rat femoral fracture model was used to test the efficacy of a single injection of BMP-2 and GDF-5. Rats were injected once with either BMP-2 at 28 µg, GDF-5 at 42 µg and GDF-5 at 100 µg or a control in the form of PBS. Both the BMP-2 and the GDF-5 were dissolved in a suitable solution and a total of 100 µL of reconstituted solution was injected locally through a 21-gauge needle that was directed into the fracture site at the time of injury. The biomechanical testing by a 3-point bending of the fractured femur was performed at four weeks post injection. Maximal load was used as an outcome measure of bone strength and fracture healing to compare the efficacy of treatments. FIG. 4 is a graph depicting the percentage increase in maximal load of BMP-2 at 28 µg, GDF-5 at 42 µg and GDF-5 at 100 µg compared to the non-treated control PBS. The data in the graph is shown as means of percentage in maximal load over the control (N=6 or 8 and *P<0.05). Results indicated that the BMP-2 was the most effective single injection relative to the GDF-5 at 42 µg and 100 µg and the PBS control.

Figure 3:
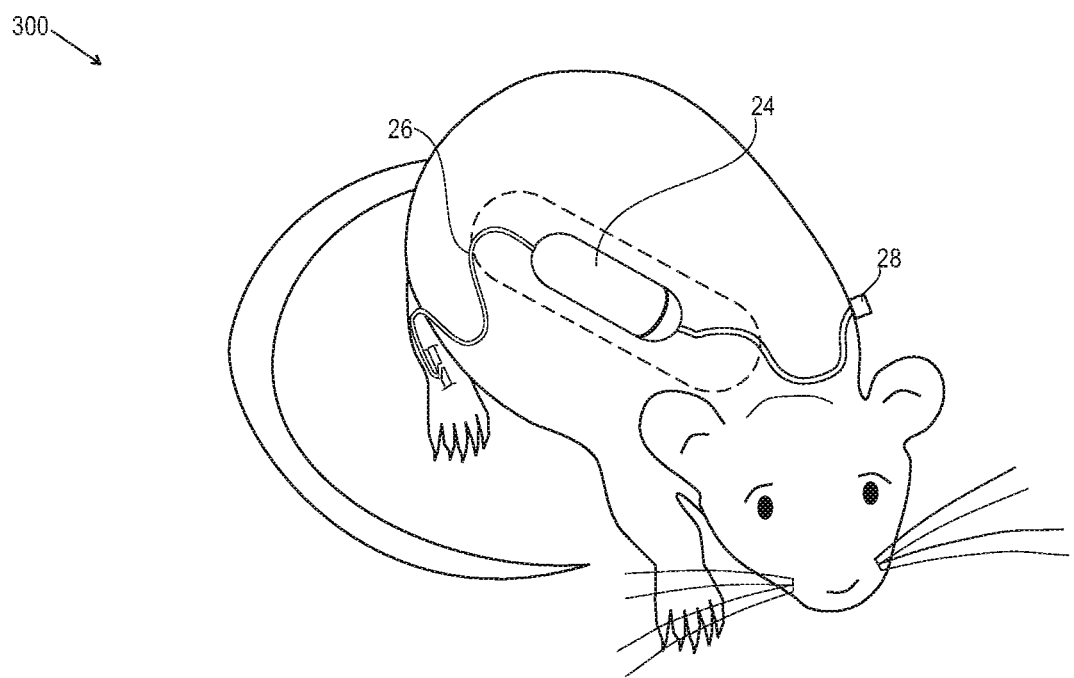
FIG. 3 is an illustration of a rat that has been implanted with a pump for administration of the GDF-5 to a bone defect. The pump includes a catheter that is positioned at the bone defect to administer the GDF-5 to the bone defect.
Figure 5:
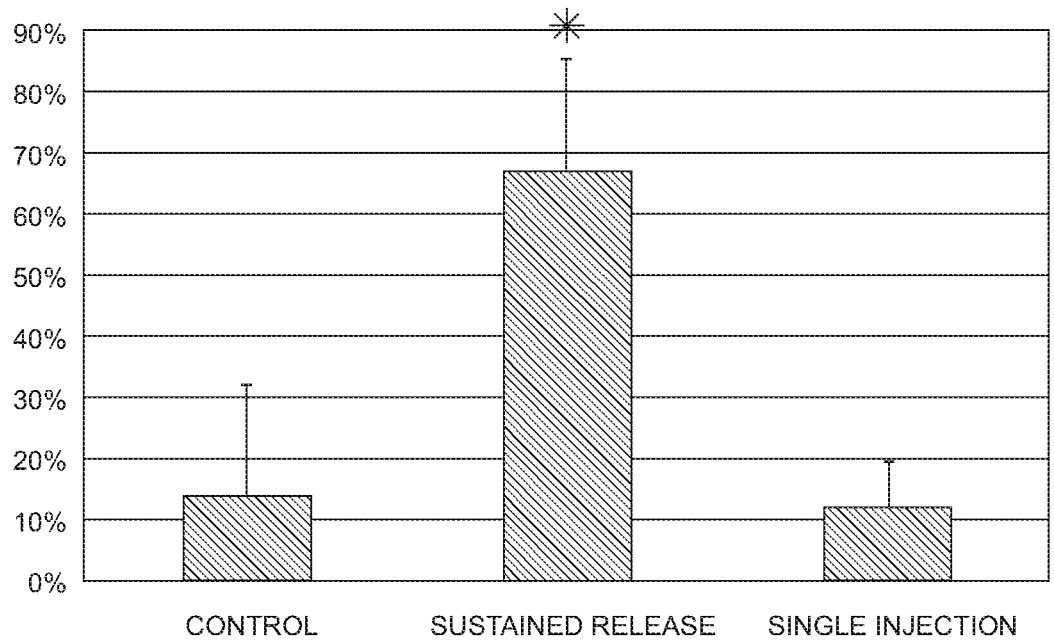
FIG. 5 is a graph depicting the percentage increase in maximal load at a bone defect (e.g., bone fracture) when a single injection of GDF-5 is administered to the bone compared to local sustained release administration of GDF-5 to the bone compared to a non-treated control. More particularly, a rat femoral fracture model was used to test the efficacy of GDF-5. A total dose of 42 μg of GDF-5 was delivered directly into the fracture site using two approaches, sustained release and a single injection. Sustained release delivery was achieved by an Alzet® pump with a catheter embedded at the injury site at a particular delivery rate and can be used as a predictable model for delivery of GDF-5 through a sustained release matrix (e.g., polymer matrix). A single bolus injection of GDF-5 was given through a needle into the fracture site. Maximal load was applied to the bone and was used as an outcome measure of bone strength and fracture healing.

As shown in FIG. 3, a rat femoral fracture model was used to test the efficacy of GDF-5. Rats 300 were either implanted with a pump 24 containing 42 µg GDF-5, were injected with 42 µg of GDF-5 or were injected with a PBS control. A total dose of 42 µg was delivered directly into the fracture site using the two approaches, sustained release (e.g., the pump) and the single injection. The pump used was an Alzet® pump with a catheter embedded at the injury site at a particular delivery rate of 3 µg/day for 14 days. A single bolus injection was performed through a needle into the fracture site. The biomechanical testing by a 3-point bending of the fractured femur was performed at four weeks post injury. Maximal load was used as an outcome measure of bone strength and fracture healing to compare the efficacy of treatments. FIG. 5 is a graph depicting the percentage increase in maximal load of GDF-5 single injection verse sustained release over the non-treated control. The data in the graph is shown as means of percentage in maximal load over the control (N=6 or 8 and *P<0.05). Results showed that sustained release of the GDF-5 performed the best having about a 65% increase in maximal load.

It should be understood that the forgoing relates to exemplary embodiments of the disclosure and that modifications may be made without departing from the spirit and scope of the disclosure as set forth in the following claims.

What is claimed is:

1. A method of treating a bone defect, the method comprising administering to the bone defect growth differentiation factor 5 (GDF-5), wherein the GDF-5 is in an aqueous carrier having a pH of from about 4.0 to about 6.0, the aqueous carrier comprising a buffering agent at a concentration from about 20 mM to 100 mM, and wherein the GDF-5 is administered by an implantable pump at a delivery rate of 3 µday for 14 days.

2. The method of claim 1, wherein the aqueous carrier comprises saline, dextrose, sterile water for injection, blood, or a combination thereof.

3. The method of claim 1, wherein the GDF-5 is administered in an amount of about 20µg to fuse the bone defect.

4. A method of treating a bone defect, the method comprising inserting an implantable medical device at, near or in the bone defect, the implantable medical device comprising growth differentiation factor 5 (GDF-5) and configured to release the GDF-5 to the bone defect, wherein the GDF-5 is in an aqueous carrier having a pH of from about 4.0 to about 6.0, the aqueous carrier comprising a buffering agent at a concentration from about 20 mM to 100 mM, and wherein the GDF-5 is administered by the implantable medical device at a delivery rate of 3 µg/day for 14 days.

5. The method of claim 4, wherein the bone defect is a fracture.

6. The method of claim 4, wherein the implantable medical device comprises an implantable pump loaded with the GDF-5.

7. The method of claim 4, wherein the GDF-5 is released in an amount of about 20 ug to fuse the bone defect.

\* \* \* \* \*